US006835537B1

(12) United States Patent
Tusneem et al.

(10) Patent No.: US 6,835,537 B1
(45) Date of Patent: Dec. 28, 2004

(54) METHOD FOR EQUALIZING BAND INTENSITIES ON SEQUENCING GELS

(75) Inventors: Nadeem Tusneem, West Jordan, UT (US); Dmitry Pruss, Salt Lake City, UT (US); Min-Jui Richard Shen, San Diego, CA (US); Satish K. Bhatnagar, Sandy, UT (US)

(73) Assignee: Myriad Genetics, Inc., Salt Lake City, UT (US)

( * ) Notice: Subject to any disclaimer, the term of this patent is extended or adjusted under 35 U.S.C. 154(b) by 941 days.

(21) Appl. No.: 09/721,918

(22) Filed: Nov. 27, 2000

Related U.S. Application Data (60) Provisional application No. 60/236,179, filed on Sep. 29, 2000.

(51) Int. Cl.[7] .................................................. C12Q 1/68
(52) U.S. Cl. ............................. 435/6; 204/451; 204/456
(58) Field of Search ................................ 204/451, 455, 204/456, 452, 461, 466, 467; 435/6, 91.1

(56) References Cited

U.S. PATENT DOCUMENTS

| 4,962,020 A | 10/1990 | Tabor et al. |
| 5,006,210 A | 4/1991 | Yueng et al. |
| 6,013,488 A | 1/2000 | Hayashizaki |
| 6,030,814 A | 2/2000 | Jendrisak |

OTHER PUBLICATIONS

S. Tabor and C. Richardson "DNA sequence analysis with a modified bacteriophage DNA polymerase" Proceedings of the National Acadeny of Sciences (USA), (Jul. 1987), vol. 84, No. 14, 4767–4771.*
Ambartsumyan et al., Elimination of the Secondary Structure Effect in Gel Sequencing of Nucleic Acids, FEBS Lett 114(2):265–8, 1980.
Ausubel, "DNA Sequencing by the Dideoxy Method," Chapter 7, DNA Sequencing, Current Protocols in Molecular Biology, John Wiley & Sons, Inc., 1999. (20 pages).
Bankier and Barrell, Shotgun DNA Sequencing, Techniques in Life Sciences, B5:Nucleic Acid Biochemistry (R.A. Flavell, ed.), pp. 1–34, Elsevier/North Holland, Limerick, Ireland, 1983.
Boyer et al., "Analysis of Mutations at Position 184 in Reverse Transcriptase of Human Immunodeficiency Virus Type 1," Antimicrobial Agents and Chemotherapy 39(7):1624–1628, Jul. 1995.

Hayatsu, "Bisulfite Modification of Nucleic Acids and Their Constituents," Prog Nucleic Acid Res Mol Biol 16:75–124, 1976.
Jensen et al., "Improvements in the chain–termination method of DNA sequencing through the use of 7–deaza–2'–deoxyadenosine," J. DNA Seq 1(4):233–9, 1991.
Li et al., "Elimination of band compression in the sequencing gels by the use of $N^4$–methyl–2'–deoxycytidine 5'–triphosphate," Nucleic Acids Res. 21(11):2709–14, Jun. 11, 1993.
McCrea et al., "Gel Compressions and Artifact Banding Can Be Resolved in the Same DNA Sequence Reaction," Biotechniques 15(5):843–844, 1993.
Mills et al., "Structure–independent nucleotide sequence analysis," Proc. Natl. Acad. Sci. USA 76(5):2232–5, May 1979.
Mizusawa et al., "Improvement of the dideoxy chain termination method of DNA sequencing by use of deoxy–7–deazaguanosine triphosphate in place of dGTP," Nucleic Acids Res. 14(3):1319–24, Feb. 11, 1986.
Rochleleau et al., "Formamide modified polyacrylamide gels for DNA sequencing by capillary gel electrophoresis," Electrophoresis 13(8):484–6, Aug. 1992.
Strahl et al., "The effects of nucleoside analogs on telomerase and telomeres in Tetrahymena," Nucleic Acids Res 22(6):893–900, Mar. 25, 1994.
Tabor et al., "DNA sequence analysis with a modified bacteriophage T7 DNA polymerase," Proc. Natl. Acad. Sci. USA 84(14):4767–71, Jul. 1987.

* cited by examiner

Primary Examiner—Nam Nguyen
Assistant Examiner—John S. Starsiak, Jr.

(57) ABSTRACT

A method for normalizing the intensity of G bands in sequencing methods which utilize dITP is presented. The use of dITP normally results in decreased intensities of G bands which occur after A bands, i.e., in the sequence AG. It has been discovered that the use of ddITP in place of ddGTP or in conjunction with ddGTP helps to normalize the intensity of the G bands following A bands. This aids in preventing errors in reading sequencing chromatograms and allows for extended reads of sequencing chromatograms as compared to methods which utilize dITP without the use of ddITP.

6 Claims, 5 Drawing Sheets

METHOD FOR EQUALIZING BAND INTENSITIES ON SEQUENCING GELS

CROSS REFERENCE TO RELATED APPLICATIONS

This is related to Ser. No. 60/236,179, filed 29 Sep. 2000, and claims benefit of the filing of said application which is incorporated herein by reference.

BACKGROUND OF THE INVENTION

Resolution of DNA sequences by the method of Sanger et al. (1977) (the publications and other materials used herein to illuminate the background of the invention or provide additional details respecting the practice, are incorporated by reference, and for convenience are respectively grouped in the appended List of References) becomes difficult in regions of dyad symmetry with high G+C content. These regions form secondary structures within the dideoxy-terminated product resulting in gel compressions during electrophoresis. Replacing deoxyguanosine triphosphate (dGTP) with deoxyinosine triphosphate (dITP) alleviates this problem (Tabor and Richardson, 1987). dGTP-dCTP forms three hydrogen bonds whereas dITP-dCTP forms two hydrogen bonds (Mills and Kramer, 1979). A number of other compounds have also been used to remove compressions. These include 7-deaza-2'-deoxyguanosine-5'-triphosphate (Mizusawa et al., 1986) (which like dITP is also used in place of dGTP) and N-4-methyl-2'-deoxycytidine-5'-triphosphate, which is used in place of deoxycytidine triphosphate (dCTP) (Li et al., 1993). Using 7-deaza-ATP with 7-deaza-GTP has also been shown to help reduce compressions (Jensen et al., 1991). However, these components in sequencing reactions have not been as effective as dITP in reducing compressions or have resulted in appearance of banding artifacts caused by premature termination (Li et al., 1993; Ausubel et al., 1999).

Non-biochemical methods have also been suggested in alleviating compressions and have resulted in a lesser degree of success than have biochemical means. The most common non-biochemical method is to add formamide to sequencing gels in order to promote denaturation of secondary structures as dideoxy-terminated molecules migrate through the gel (Rocheleau et al., 1992). A second method for removing compressions requires running a sequencing gel at higher temperatures than the temperature at which they are commonly run (Ausubel et al., 1999). However, this approach is not widely used as glass gel plates crack at higher temperatures and resolution suffers. Another method, not widely used, is to modify the C residues chemically so they can no longer form GC base pairs. This can be accomplished by treating the sequencing products with bisulfite or a mixture of bisulfite and methoxyamine (Ambartsumyan and Mazo, 1980; Hayatsu, 1976).

The best candidate for removal of compressions is dITP which is widely used. A number of problems have been associated with use of dITP and solutions have been suggested in the literature. First, the rate of dITP incorporation is slower than is the rate of dGTP incorporation causing the reaction to terminate quickly thereby resulting in inability to resolve bases far from the primer (McCrea et al., 1993). To overcome this problem, ddGTP concentration can be reduced in the mixture. A second problem associated with dITP is that while the sequencing enzyme uses dITP efficiently, it has a tendency to stall in sequencing reactions and produce sequencing ladders that have a higher frequency of bands in all four lanes (as in the case of use of radioactive labels). Adding terminal deoxynucleotidyl transferase to the reaction can eliminate this problem (Fawcett and Bartlett, 1990).

Figure 1:
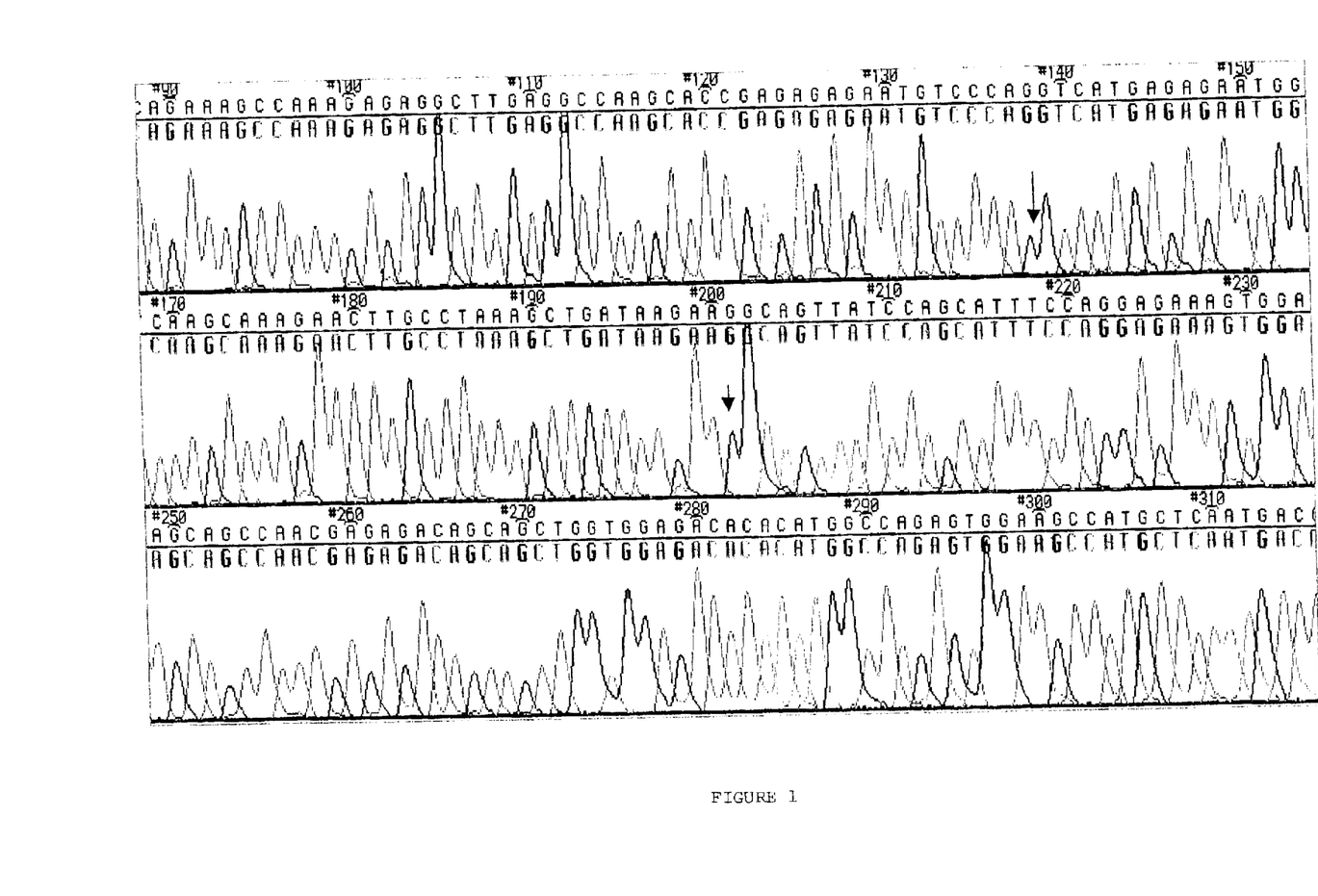
FIG. 1 is a sequencing chromatogram from a dye terminator sequencing reaction showing the results of a reaction utilizing dITP with ddGTP and illustrating the decreased intensity of G peaks following A peaks.

Another significant and yet unresolved problem associated with the use of dITP is the frequent decrease in amplitude of G peaks following an A peak (FIG. 1). Also, the amplitude of G in a string of two or more Gs is low. This is most noticeable when the first G is preceded by an A. This results in problems in resolution of G peaks far from the primer and in reactions where the overall signal intensity is low and could result in erroneous base calling. This phenomenon has been observed both in dye terminator and dye primer sequencing chemistries. An explanation for this result could be that dITP gets incorporated at a higher frequency than does ddGTP after dATP has been incorporated.

SUMMARY OF THE INVENTION

In DNA sequencing reactions which utilize dITP to minimize band compressions on gels, ddITP or a combination of ddITP and ddGTP as chain terminators in sequencing reactions is used to increase the amplitude of G peaks following A peaks. This use of ddITP or combination of ddITP with ddGTP results in the G peaks which follow A peaks being of greater amplitude than they are in the absence of using ddITP and more similar to the amplitude of neighboring peaks thereby allowing longer and more accurate reads of each sequencing gel.

BRIEF DESCRIPTION OF THE FIGURES

The file of this patent contains at least one drawing executed in color. Copies of this patent with color drawings will be provided by the Patent and Trademark Office upon request and payment of the necessary fee.

DETAILED DESCRIPTION OF THE INVENTION

The interpretation of DNA sequences by the method of Sanger et al. (1977) can be difficult at areas of dyad symmetry rich in G+C content. These regions can produce secondary structures within the dideoxy-terminated product resulting in gel compressions during electrophoresis. A variety of methods have been used to eliminate compressions including substitution of dITP or 7-deaza-2'-deoxyguanosine-5'-triphosphate for dGTP and N-4 methyl-2'-deoxycytidine-5'-triphosphate for dGTP to reduce the number of hydrogen bonds between G and C residues. 7-deaza-dATP in combination with 7-deaza-dGTP is also useful in resolving compressions. However some of these reactions tend to have banding artifacts caused by premature termination of the polymerase. Other suggestions involve running sequencing gels at the highest possible temperature or inclusion of formamide in the sequencing gel to promote denaturation of secondary structures. Another method not widely used is to chemically modify C residues so that they can no longer engage in the formation of G-C base pairs.

The most widely used method for minimizing gel band compressions on sequencing gels is to use dITP in place of dGTP. Although this method eliminates many of the band compressions, it results in a new problem, this being that the amplitude (as measured on sequencing gels using fluorescent labels) of G bands is relatively small as compared to neighboring bands when the G immediately follows an A. This decreased amplitude increases the possibility that the G band will be overlooked, especially when the sequence is far from the primer and the intensities (amplitudes) of all bands are decreasing. The present disclosure teaches the use of ddITP in the G termination reaction to overcome this problem.

Use of ddITP in research has been limited to study of viral polymerase activities (Boyer and Hughes, 1995; Strahl and Blackburn, 1994). The only comment regarding ddITP and sequencing in the literature is that ddGTP, and not ddITP, should be used in sequencing reactions (Bankier and Barrell, 1983). In the present disclosure, it is shown that ddITP can be used in sequencing reactions along with dITP to overcome the decreased G band intensity which occurs with the sequence AG. Furthermore, a mixture of ddITP and ddGTP in the G termination sequencing reaction can also be used.

Several different kits are commercially available for performing sequencing. The problems discussed above concerning band compressions on sequencing gels and decreased peak intensity will appear to varying extents with these kits. These kits can be modified to use ddITP or a combination of ddITP and ddGTP to aid in minimizing these problems.

The following Examples illustrate the method of incorporating ddITP into sequencing reactions to help equalize the intensities of G bands which follow A bands with the intensities of the bands neighboring the G bands. It should be noted that the products obtained from the sequencing reactions using the invention can be analyzed by any appropriate means, e.g., the products can be electrophoresed on a polyacrylamide gel or they can be analyzed by use of capillary tubes. The present invention is further detailed in the following Examples, which are offered by way of illustration and are not intended to limit the invention in any manner. Standard techniques well known in the art or the techniques specifically described below are utilized.

EXAMPLE 1

Illustration of the Prior Art Problems

Sequencing reactions using dITP in place of dGTP in order to remove compressions have a very characteristic phenomenon. This phenomenon was observed in dye terminator sequencing using the PE dye terminator kit (FIG. 1). The amplitudes of G following an A are reduced. Also notice that the first G peak following an A peak has a lower amplitude than does the second G peak. This problem was also noticed in sequencing reactions using dye primer chemistry during experiments aimed at reducing compressions. Two sets of experiments were set up simultaneously. Experiment 1A involved four reactions using dGTP, dATP, dCTP, and dTTP as deoxyribonucleotides for extension (Table 1A). Experiment 1B used dITP, dATP, dCTP, and dTTP as the deoxyribonucleotides for extension (Table 1B). The terminating dideoxynucleotide for the G reaction was ddGTP and was used in both sets of experiments.

TABLE 1A

Reaction Conditions for dGTP and ddGTP Sequencing Reactions

| Experiment Set 1A | "G" termination reaction | "A" termination reaction | "T" termination reaction | "C" termination reaction |
|---|---|---|---|---|
| dGTP, dATP, dTTP, dCTP | 45 μM | 45 μM | 45 μM | 45 μM |
| ddGTP | 0.37 μM | — | — | — |
| ddATP | — | 0.37 μM | — | — |
| ddTTP | — | — | 0.37 μM | — |
| ddCTP | — | — | — | 0.37 μM |
| Taq FS Polymerase | 0.225 units/μL | 0.225 units/μL | 0.225 units/μL | 0.225 units/μL |
| "G" Big Dye primer | 40 μM | — | — | — |
| "A" Big Dye primer | — | 40 μM | — | — |
| "T" Big Dye primer | — | — | 40 μM | — |
| "C" Big Dye primer | — | — | — | 40 μM |
| Sequencing Buffer | 1X | 1X | 1X | 1X |
| Template | 10 ng | 10 ng | 10 ng | 10 ng |

TABLE 1B

Reaction Conditions for dITP and ddGTP Sequencing Reactions

| Experiment Set 1B | "G" termination reaction | "A" termination reaction | "T" termination reaction | "C" termination reaction |
|---|---|---|---|---|
| dITP, dATP, dTTP, dCTP | 45 μM | 45 μM | 45 μM | 45 μM |
| ddGTP | 0.07 μM | — | — | — |

TABLE 1B-continued

Reaction Conditions for dITP and ddGTP Sequencing Reactions

| Experiment Set 1B | "G" termination reaction | "A" termination reaction | "T" termination reaction | "C" termination reaction |
|---|---|---|---|---|
| ddATP | — | 0.37 µM | — | — |
| ddTTP | — | — | 0.37 µM | — |
| ddCTP | — | — | — | 0.37 µM |
| Taq FS Polymerase | 0.225 units/µL | 0.225 units/µL | 0.225 units/µL | 0.225 units/µL |
| "G" Big Dye primer | 40 µM | — | — | — |
| "A" Big Dye primer | — | 40 µM | — | — |
| "T" Big Dye primer | — | — | 40 µM | — |
| "C" Big Dye primer | — | — | — | 40 µM |
| Sequencing Buffer | 1X | 1X | 1X | 1X |
| Template | 10 ng | 10 ng | 10 ng | 10 ng |

Figure 2A:
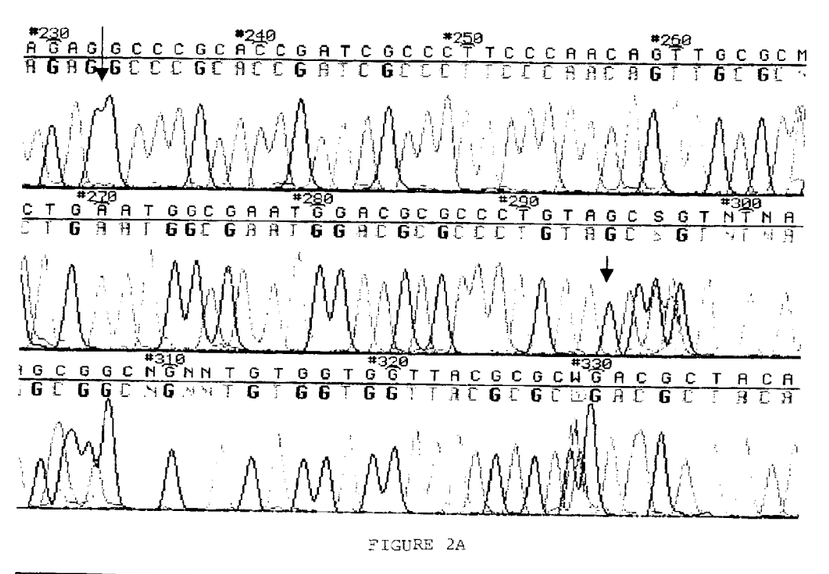
FIG. 2A is a sequencing chromatogram showing the results of a reaction utilizing dGTP and ddGTP (Experiment 1A) and illustrating the presence of band compressions.
Figure 2B:
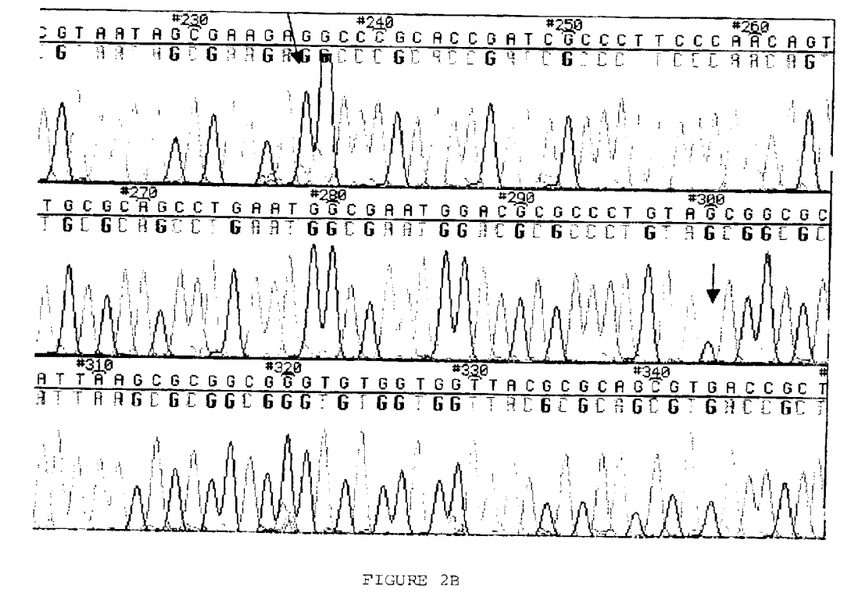
FIG. 2B is a sequencing chromatogram showing the results of a reaction utilizing dITP and ddGTP (Experiment 1B) and illustrating that the band compressions of FIG. 2A are eliminated but at the cost of decreased intensity of G peaks following A peaks.
Figure 4A:
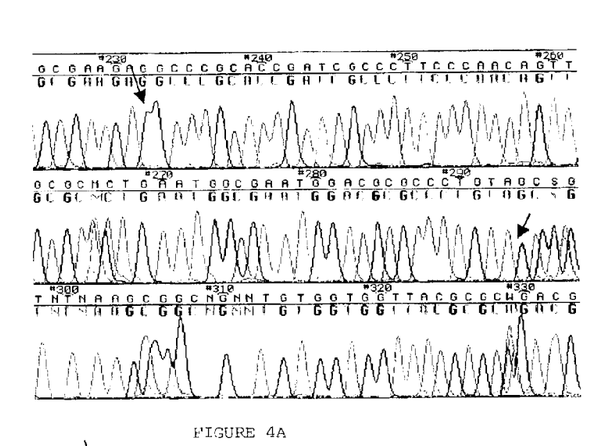
FIG. 4A is a sequencing chromatogram showing the results of a reaction utilizing dGTP and ddGTP (Experiment 1A) illustrating the presence of compressions but with relatively even peak intensities in the regions without compressions.
Figure 4B:
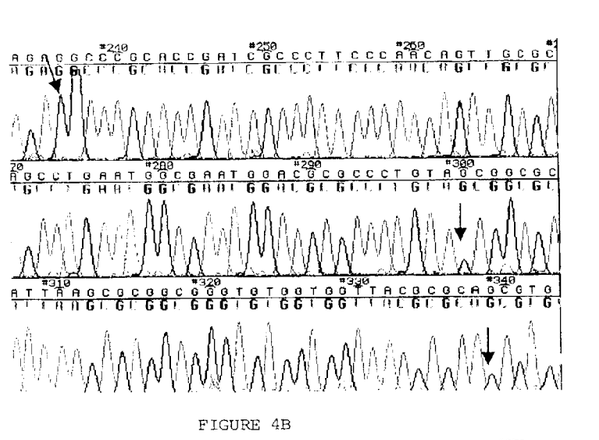
FIG. 4B is a sequencing chromatogram showing the results of a reaction utilizing dITP and ddGTP (Experiment 1B) illustrating the minimization of band compressions but at the cost of decreased G peak intensities following A bands.
Figure 4C:
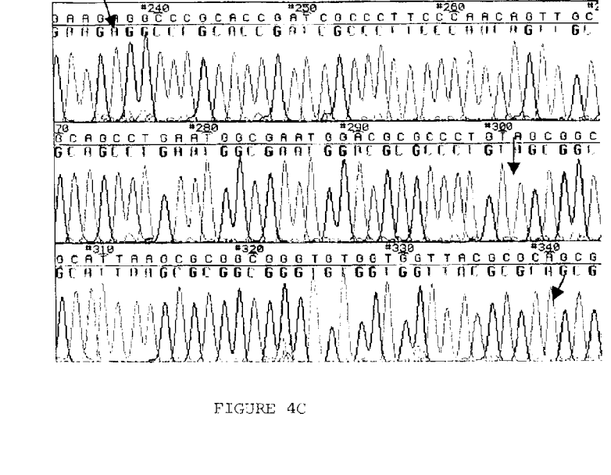
FIG. 4C is a sequencing chromatogram showing the results of a reaction utilizing dITP and ddITP (Experiment 2B) illustrating the minimization of band compressions while overcoming the decrease of G peak intensities following an A peak.
Figure 4D:
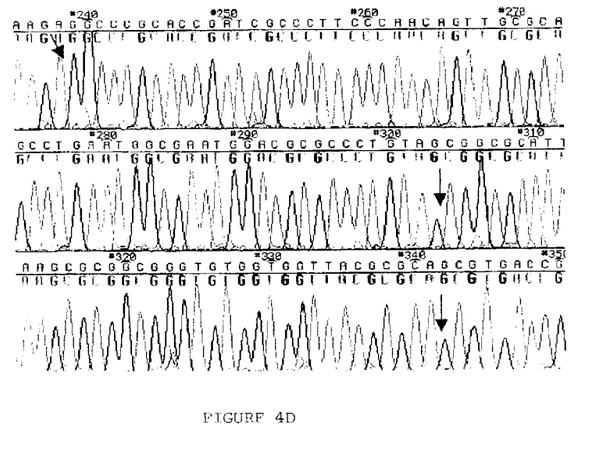
FIG. 4D is a sequencing chromatogram showing the results of a reaction utilizing dITP and ddITP plus ddGTP (Experiment 3) illustrating the minimization of band compressions while obtaining even G peaks following A peaks as compared to FIG. 4B.
Figure 5A:
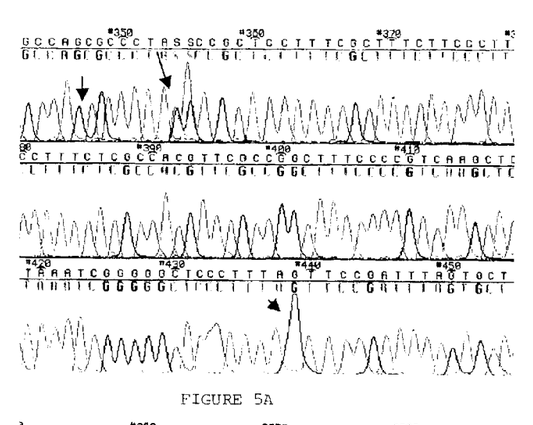
FIGS. 5A–D are sequencing chromatograms of the same template as in FIGS. 4A–D except that a different region is shown.
Figure 5B:
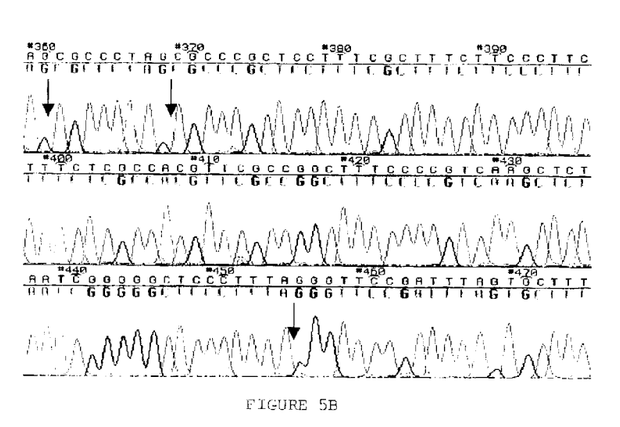
Figure 5C:
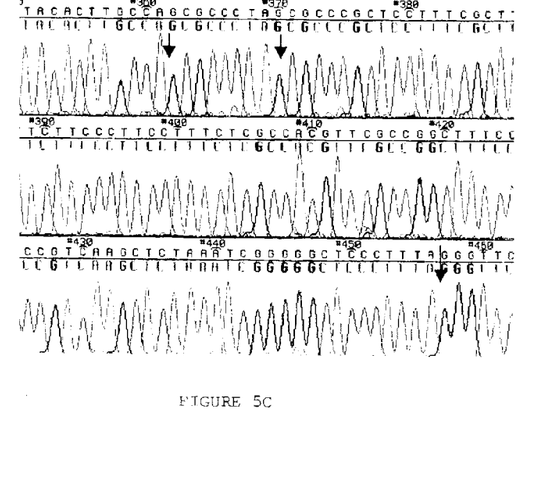
Figure 5D:
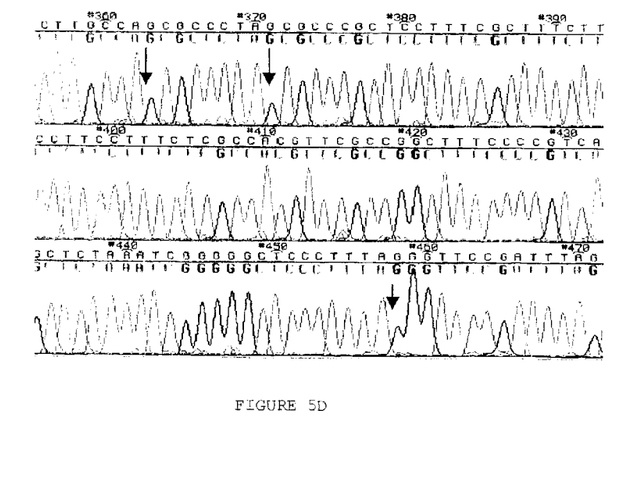

The composition of the 1X sequencing buffer used in all of the experiments in this disclosure is 50 mM Tris-HCl pH 9.0, 3 mM $MgCl_2$, and 0.01% Tween 20. The "Big Dye Primers" are from Perkin Elmer Biosystems (Foster City, Calif.). The reactions were cycle-sequenced for 32 cycles (94° C. for 30 seconds, 50° C. for 30 seconds, and 60° C. for 3 minutes). The four termination reactions from Experiment 1A were consolidated and precipitated with 70% ethanol. The same was repeated for the four sequencing reactions containing dITP as shown in Table 1B. The pellets were resuspended in 10 µL water prior to loading on to capillaries. Samples were run on a MegaBace capillary sequencer and data was analyzed using Myriad Genetics sequencing software. Results of the experiments are shown in FIGS. 2A, 2B, 4A, 4B, 5A and 5B. Sequencing reactions using dGTP show compressions and show no variation in amplitudes of "G" peaks (FIGS. 2A, 4A and 5A). Sequencing reactions using dITP resolve the compressions but show variation in "G" peak heights that are incorporated after dATP, suggesting a preference of incorporation of dITP over ddGTP after an incorporation of dATP (FIGS. 2B, 4B and 5B).

EXAMPLE 2

DNA Sequencing Reactions Using ddITP

In this experiment ddGTP was replaced with ddITP in dye primer sequencing reactions. ddITP was used with dNTP mixtures containing dGTP or dITP. For each set of experiments, four termination reactions were set up (labeled "G", "A", "T", and "C"). ddITP was used in Experiment 2A with dGTP as the extension deoxyribonucleotide and in Experiment 2B with dGTP as the extension deoxyribonucleotide. Setup of reactions is described in Tables 2A and 2B.

TABLE 2A

Reaction Conditions for Sequencing Reactions Involving dGTP and ddITP

| Experiment Set 2A | "G" termination reaction | "A" termination reaction | "T" termination reaction | "C" termination reaction |
|---|---|---|---|---|
| dGTP, dATP, dTTP, dCTP | 45 µM | 45 µM | 45 µM | 45 µM |

TABLE 2A-continued

Reaction Conditions for Sequencing Reactions Involving dGTP and ddITP

| Experiment Set 2A | "G" termination reaction | "A" termination reaction | "T" termination reaction | "C" termination reaction |
|---|---|---|---|---|
| ddITP | 0.37 MM | — | — | — |
| ddATP | — | 0.37 µM | — | — |
| ddTTP | — | — | 0.37 µM | — |
| ddCTP | — | — | — | 0.37 µM |
| Taq FS Polymerase | 0.225 units/µL | 0.225 units/µL | 0.225 units/µL | 0.225 units/µL |
| "G" Big Dye primer | 40 µM | — | — | — |
| "A" Big Dye primer | — | 40 µM | — | — |
| "T" Big Dye primer | — | — | 40 µM | — |
| "C" Big Dye primer | — | — | — | 40 µM |
| Sequencing Buffer | 1X | 1X | 1X | 1X |
| Template | 10 ng | 10 ng | 10 ng | 10 ng |

TABLE 2B

Reaction Conditions for Sequencing Reactions Involving dITP and ddITP

| Experiment Set 2B | "G" termination reaction | "A" termination reaction | "T" termination reaction | "C" termination reaction |
|---|---|---|---|---|
| dITP, dATP, dTTP, dCTP | 45 µM | 45 µM | 45 µM | 45 µM |
| ddTTP | 0.37 µM | — | — | — |
| ddATP | — | 0.37µM | — | — |
| ddTTP | — | — | 0.37µM | — |
| ddCTP | — | — | — | 0.37 µM |
| Taq FS Polymerase | 0.225 units/µL | 0.225 units/µL | 0.225 units/µL | 0.225 units/µL |
| "G" Big Dye primer | 40 µM | — | — | — |
| "A" Big Dye primer | — | 40 µM | — | — |
| "T" Big Dye primer | — | — | 40 µM | — |
| "C" Big Dye primer | — | — | — | 40 µM |
| Sequencing Buffer | 1X | 1X | 1X | 1X |
| Template | 10 ng | 10 ng | 10 ng | 10 ng |

Figure 3A:
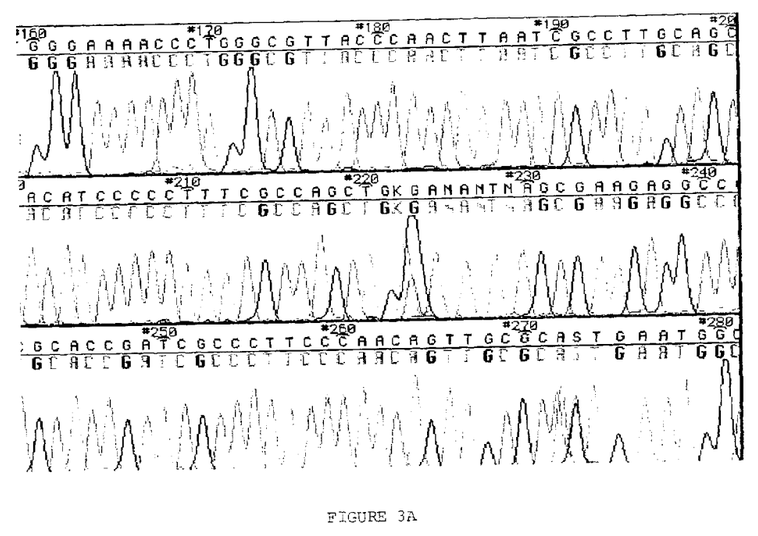
FIG. 3A is a sequencing chromatogram showing the results of a reaction utilizing dGTP few and ddITP (Experiment 2A) illustrating that ddITP is not useful for eliminating band compressions.
Figure 3B:
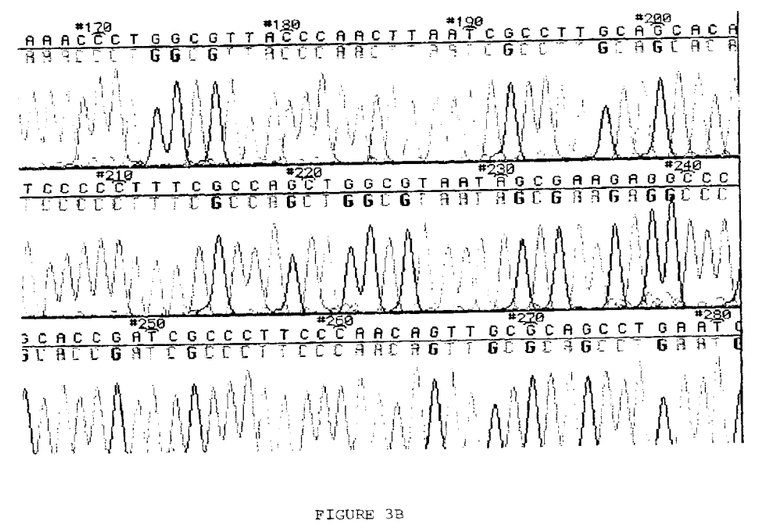
FIG. 3B is a sequencing chromatogram showing the results of a reaction utilizing dITP and ddITP (Experiment 2B) illustrating that this combination minimizes band compressions and also helps to normalize the intensity of G peaks following A peaks.

The reactions were cycle sequenced for 32 cycles (94° C. for 30 seconds, 50C for 30 seconds, and 60° C. for 3 minutes). The four termination reactions from each of Experiments 2A and 2B were pooled and precipitated as described for Experiment 1. Samples were run on a MegaBace capillary sequencer and data were analyzed using Myriad Genetics sequencing software. The combination of dGTP and ddITP did not resolve compressions (FIG. 3A). The combination of dITP and ddITP resulted in resolution of compressions (FIG. 3B) and showed sequencing quality similar to that obtained using dITP and ddGTP but with more even G intensities (compare FIG. 4B to FIG. 4C and FIG. 5B to FIG. 5C). The insertion of ddGTP after dATP was not affected as was seen in the case of sequencing with dITP and ddGTP Experiment 1B). However, there is a slight decrease in G intensity following a T.

EXAMPLE 3

Use of ddITP and ddGTP Mixture in Sequencing Reactions

In order to increase the amplitude of "G" peaks after "A" and/or "T" peaks, a combination of ddGTP and ddITP was used to terminate G reactions in sequencing. For Experiment 3, four sets of G, A, T and C reactions were prepared as described in Table 3 below. The reactions were then cycle-sequenced for 32 cycles (94° C. for 30 seconds, 50° C. for 30 seconds, and 60° C. for 3 minutes). The four termination reactions from Experiment 3 were consolidated and precipitated with 70% ethanol as described above. The pellets were resuspended in 10 μL water. Samples were run on a Megabace capillary sequencer and data were analyzed using Myriad Genetics sequencing software.

TABLE 3

Experiental Conditions for dITP and ddITP/ddGTP Sequencing Reactions

| Experiment Set 2B | "G" termination reaction | "A" termination reaction | "T" termination reaction | "C" termination reaction |
|---|---|---|---|---|
| dITP, dATP, dTTP, dCTP | 45 μM | 45 μM | 45 μM | 45 μM |
| ddITP | 0.18 μM | — | — | — |
| ddATP | — | 0.37 μM | — | — |
| ddTTP | — | — | 0.37 μM | — |
| ddCTP | — | — | — | 0.37 μM |
| ddGTP | 0.035 μM | — | — | — |
| Taq FS Polymerase | 0.225 units/μL | 0.225 units/μL | 0.225 units/μL | 0.225 units/μL |
| "G" Big Dye primer | 40 μM | — | — | — |
| "A" Big Dye primer | — | 40 μM | — | — |
| "T" Big Dye primer | — | — | 40 μM | — |
| "C" Big Dye primer | — | — | — | 40 μM |
| Sequencing Buffer | 1X | 1X | 1X | 1X |
| Template | 10 ng | 10 ng | 10 ng | 10 ng |

The results of this experiment are presented in FIGS. 4 and 5 (these show different regions of the same sequencing runs). In Experiment 3 (dITP+ddITP+ddGTP), the reduction of amplitude of the G peak after A or T incorporation was less (FIGS. 4D and 5D) as compared to Experiment 2B (dITP+ddITP; FIGS. 4C and 5C) and Experiment 1B (dITP+ddGTP; FIGS. 4B and 5B), ie., the intensity of the G bands was more even to the neighboring bands. This result allows one to read longer sequences than can be read in the absence of ddITP because the G intensity is increased and the G bands are not lost in the background as readily as the signal begins to fade, especially at long distances from the primer sequence.

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

LIST OF REFERENCES

Ambartsumyan NS and Mazo AM (1980). FEBS Lett 114:265–268.

Ausubel FM, et al. (eds.) (1999). *Current Protocols in Molecular Biology.* Chapter 7: DNA Sequencing. Unit 7.4A: DNA Sequencing by the dideoxymethod. (John Wiley and Sons, Inc., New York).

Bankier AT and Barrell BG (1983). *Techniques in Life Sciences, B5: Nucleic Acid Biochemistry* (RA Flavell, ed.), pp. 1–34 (Elsevier/North Holland, Limerick, Ireland).

Boyer PL and Hughes SH (1995). Antimicrob. Agents Chemother. 39:1624–1628.

Fawcett TW and Bartlett SG (1990). Biotechniques 7:700–708.

Hayatsu H (1976). Prog Nucl. Acid Res. Mol. Biol. 16:75–124.

Jensen MA, et al. (1991). DNA Seq. 1:233–239.

Li S, et al. (1993). Nucl. Acids Res. 21:2709–2714.

McCrea KW, et al. (1993). Biotechniques 15:843–844.

Mills DR and Kramer FR (1979). Proc. Natl. Acad. Sci. USA 76:2232–2235.

Mizusawa S, et al. (1986). Nucl. Acids Res. 14:1319–1324.

Rocheleau MJ, et al. (1992). Electrophoresis 13.484–486.

Sanger F, et al. (1977). Proc. Natl. Acad. Sci. USA 74:5463–5467.

Strahl C and Blackburn EH (1994). Nucl. Acids Res. 22:893–900.

Tabor S and Richardson C (1987). Proc. Nail. Acad. Sci. USA 84:4767–4771.

What is claimed is:

1. A method using the intensity of a G band in a sequencing analysis when said G band immediately follows an A band, comprising utilizing ddITP in a sequencing reaction which includes dITP and analyzing said sequencing reaction.

2. The method of claim 1 wherein ddITP is utilized in the absence of ddGTP.

3. The method of claim 1 wherein ddITP is utilized together with ddGTP.

4. The method of claim 1 wherein said sequencing reaction utilizes Taq FS polymerase.

5. The method of claim 1 wherein said analyzing is by gel electrophoresis.

6. The method of claim 1 wherein said analyzing is by capillary electrophoresis.

\* \* \* \* \*

UNITED STATES PATENT AND TRADEMARK OFFICE
CERTIFICATE OF CORRECTION

| | | |
|---|---|---|
| PATENT NO. | : 6,835,537 B1 | Page 1 of 1 |
| APPLICATION NO. | : 09/721918 | |
| DATED | : December 28, 2004 | |
| INVENTOR(S) | : Tusneem et al. | |

It is certified that error appears in the above-identified patent and that said Letters Patent is hereby corrected as shown below:

Claim 1, line 1, please change "using" to --for increasing--.

Signed and Sealed this

Eighteenth Day of July, 2006

JON W. DUDAS
*Director of the United States Patent and Trademark Office*